United States Patent [19]
Baugh et al.

[11] Patent Number: 6,010,911
[45] Date of Patent: *Jan. 4, 2000

[54] APPARATUS FOR PERFORMING A HEPARIN-INDEPENDENT HIGH SENSITIVITY PLATELET FUNCTION EVALUATION TECHNIQUE

[75] Inventors: Robert F. Baugh, Parker; Carole G. Lane, Greenwood Village; Adrian C. Wilson, Denver, all of Colo.

[73] Assignee: Medtronic, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/847,152

[22] Filed: Apr. 30, 1997

[51] Int. Cl.⁷ .................................................. G01N 33/16
[52] U.S. Cl. .............................. 436/69; 436/10; 436/18; 436/63; 422/73; 435/4; 435/13
[58] Field of Search .................................. 436/10, 63, 69, 436/18; 422/73; 435/4, 13

[56] References Cited

U.S. PATENT DOCUMENTS

| | | | |
|---|---|---|---|
| 3,985,618 | 10/1976 | Innerfield | 195/103.5 R |
| 4,443,408 | 4/1984 | Mintz | 422/73 |
| 4,533,519 | 8/1985 | Baugh et al. | 422/73 |
| 4,551,308 | 11/1985 | Mintz | 422/58 |
| 4,599,219 | 7/1986 | Cooper et al. | 422/61 |
| 4,671,939 | 6/1987 | Mintz | 422/58 |
| 4,720,787 | 1/1988 | Lipscomb | 364/416 |
| 4,782,026 | 11/1988 | Baugh et al. | 436/69 |
| 4,788,139 | 11/1988 | Ryan | 435/13 |
| 4,871,677 | 10/1989 | Baugh et al. | 436/69 |
| 5,093,325 | 3/1992 | Witt et al. | 514/165 |
| 5,174,961 | 12/1992 | Smith | 422/73 |
| 5,196,404 | 3/1993 | Maraganore et al. | 514/13 |
| 5,207,988 | 5/1993 | Lucas | 422/73 |
| 5,246,715 | 9/1993 | Orevi et al. | 424/550 |
| 5,248,673 | 9/1993 | Balesubramanian et al. | 514/212 |
| 5,266,462 | 11/1993 | Hemker et al. | 435/13 |
| 5,314,826 | 5/1994 | Baugh | 436/69 |
| 5,387,581 | 2/1995 | Odawara et al. | 514/165 |
| 5,441,892 | 8/1995 | Baugh | 436/69 |
| 5,472,852 | 12/1995 | Smirnov et al. | 435/13 |
| 5,510,330 | 4/1996 | Martin et al. | 514/12 |
| 5,525,477 | 6/1996 | Hassouna | 435/13 |
| 5,525,478 | 6/1996 | Matschiner | 435/13 |
| 5,563,041 | 10/1996 | Reers | 435/13 |
| 5,602,037 | 2/1997 | Ostgaard et al. | 436/69 |
| 5,607,952 | 3/1997 | Badore et al. | 514/326 |
| 5,612,369 | 3/1997 | Bone et al. | 514/423 |
| 5,612,378 | 3/1997 | Tiabao et al. | 514/602 |
| 5,637,599 | 6/1997 | Levy et al. | 514/326 |
| 5,674,236 | 10/1997 | Baugh | 606/181 |
| 5,702,912 | 12/1997 | Henker et al. | 435/13 |

OTHER PUBLICATIONS

"Heparinase in the Activated Clotting Time Assay: Monitoring Heparin–Independent Alterations in Coagulation Function," Baugh, et al., *Anesth Analg* 74:201–5 (1992).

*Primary Examiner*—Jill Warden
*Assistant Examiner*—S. Carrillo
*Attorney, Agent, or Firm*—Steven C. Petersen; Chrisman Bynum & Johnson

[57] ABSTRACT

An apparatus and method for performing activated clotting time tests, including their use for evaluating platelet functionality of a blood sample. The apparatus includes a plurality of test cells. Each of the cells comprises a heparin-inactivating agent, an anticoagulant agent, and a clotting reagent. At least one of the test cells further comprises a platelet activating agent. The clotting time is determined for each of the aliquot portions, and the relative clotting times of the aliquot portions in the cells are determinative of the platelet functionality of the sample. The method comprises the steps of combining a heparin-inactivating agent, an anticoagulant agent, a clotting reagent, a platelet activating agent, and the sample of blood to be tested to form a test mixture. The platelets of the sample are activated by agitating the test mixture, and the activated clotting time test is terminated upon detecting a predetermined change in a property of the test mixture. The activated clotting time of the sample of blood is calculated based on the elapsed time.

37 Claims, 6 Drawing Sheets

APPARATUS FOR PERFORMING A HEPARIN-INDEPENDENT HIGH SENSITIVITY PLATELET FUNCTION EVALUATION TECHNIQUE

BACKGROUND OF THE INVENTION

1. Field of the Invention

The present invention relates to measuring and detecting coagulation and coagulation-related activities in fluids, particularly human blood. More particularly, the present invention relates to an improved activated clotting time test for whole blood which provides accurate and reliable detection of coagulation-related activities regardless of the concentration of heparin in the blood. Further, this invention relates to a new and improved technique for evaluating the effects of therapeutic levels of platelet function inhibitors on the coagulation of whole blood regardless of the heparin concentration of the blood.

2. Description of the State of the Art

Blood coagulation is a complex chemical and physical reaction which occurs when blood comes into contact with an activating agent, such as an activating surface or an activating reagent. In accordance with one simplified conceptual view, the whole blood coagulation process can be generally viewed as three activities: agglutination of platelets, blood clotting, and fibrous tissue formation. In vivo, platelets flow through the blood vessels in an inactivated state because the blood vessel lining, the endothelium, prevents activation of platelets. When a blood vessel is damaged, however, the endothelium loses its inert character and platelets are activated by contact with tissue underlying the damaged site. Activation of the platelets causes them to become "sticky" and adhere together. Additional platelets then adhere to the activated platelets and also become activated. This process continues until a platelet "plug" is formed. This platelet plug then serves as a matrix upon which blood clotting proceeds.

If the chemical balance of the blood is suitable, thrombin is then produced which causes conversion of fibrinogen to fibrin, which forms the major portion of the clot mass. During clotting, additional platelets are activated and trapped in the forming clot, contributing to clot formation. As clotting proceeds, polymerization and cross-linking of fibrin serves as the permanent clot. Thus, platelet activation plays a very important function in blood coagulation.

A number of different medical apparatuses and testing methods exist for measuring and determining coagulation and coagulation-related activities of blood. These apparatuses and methods provide valuable medical information to an attending physician. For example, the information assists a physician in prescribing medication, predicting postoperative bleeding and prescribing various therapies. Some of the more successful techniques of evaluating blood clotting and coagulation are the plunger techniques illustrated by U.S. Pat. Nos. 4,599,219 to Cooper et al., 4,752,449 to Jackson et al., and 5,174,961 to Smith, all of which are assigned to the assignee of the present invention, and all of which are incorporated herein by reference.

Automated apparatuses employing the plunger technique for measuring and detecting coagulation and coagulation-related activities generally comprise a plunger sensor cartridge or cartridges and a microprocessor controlled apparatus into which the cartridge is inserted. The apparatus acts upon the cartridge and the blood sample placed therein to induce and detect the coagulation-related event. The cartridge includes a plurality of test cells, each of which is defined by a tube-like member having an upper reaction chamber where a plunger assembly is located and where the analytical test is carried out, and a reagent chamber which contains a reagent or reagents. For an activated clotting time (ACT) test, for example, the reagents include an activation reagent to activate coagulation of the blood. A plug member seals the bottom of a reagent chamber. When the test commences, the contents of the reagent chamber are forced into the reaction chamber to be mixed with the sample of fluid, usually human blood or its components. An actuator, which is a part of the apparatus, lifts the plunger assembly and lowers it, thereby reciprocating the plunger assembly through the pool of fluid in the reaction chamber. The plunger assembly descends on the actuator by the force of gravity, resisted by a property of the fluid in the reaction chamber, such as its viscosity. When the property of the sample changes in a predetermined manner as a result of the onset or occurrence of a coagulation-related activity, the descent rate of the plunger assembly therethrough is changed. Upon a sufficient change in the descent rate, the coagulation-related activity is detected and indicated by the apparatus.

Certain discoveries have recently been made which contribute to a better understanding of the role of platelets in an ACT test. Such discoveries suggest that the activation of the platelets has a significant and previously unappreciated effect on ACT test results. While it has long been suspected that platelet activation contributes to total blood coagulation times, until fairly recently, there has been no technique available for confirming and quantifying the impact of platelet activation on ACT. U.S. Pat. No. 5,312,826 to Baugh describes an improved ACT test which includes a platelet activation phase to accommodate the effects of platelet activation. In the platelet activation phase an activating reagent is mixed with a sample of blood to be tested, then the mixture is gently agitated in such a manner and for a period of time sufficient to establish a predetermined and predictable contribution to the ACT from platelet activation. To evaluate platelet function, two simultaneous ACT tests (with different platelet activation phases) are performed, and the difference between the ACTs is indicative of the platelet functionality of the sample of blood. In a further improvement, described in U.S. Ser. No. 08/640,275, filed Apr. 30, 1996, the sample of blood is mixed with a chemical platelet activating agent to facilitate the participation of active platelets in the blood clotting reaction, thereby shortening the clotting time of the blood. If the platelets are inactive or not functioning normally, the activator will have minimal or no effect on the clotting time. Both U.S. Pat. No. 5,312,826 and U.S. Ser. No. 08/640,275 are assigned to the assignee of the present invention, and are incorporated by reference in their entireties herein.

Although previous apparatuses using the plunger sensing technique have proven generally satisfactory, the need for certain enhancements has been identified. Specifically, while these techniques can measure and detect coagulation and coagulation-related activities in a sample of blood, none are designed to conveniently accommodate either heparinized or unheparinized (patient) blood in a single test cartridge. Most of the apparatuses currently available for monitoring platelet function are designed specifically for highly heparinized blood, or the test cartridge used to perform the ACT test must include a sufficient concentration of heparin to inhibit post-platelet activation (i.e., subsequent to factor XII activation) reactions. Heparin is necessary to inhibit reactions which occur later in the coagulation process, such as activation of factors X, II (prothrombin) and I (fibrinogen), i.e., reactions in the common pathway or in a later stage in the intrinsic pathway. By inhibiting these later clotting factors, heparin (which together with antithrombin III accelerates the inactivation of factor X and thrombin) helps to accentuate the contribution of platelets to clotting, which is the rate-limiting step in blood coagulation, i.e., the actual clotting times in the ACT test depend on how rapidly the platelets are able to activate clotting. Accordingly, heparin must be either present in the blood sample or included in the test cartridge to inhibit non-platelet-related reactions which tend to obscure the rate-limiting activation step.

Although heparin is effective in accentuating the platelet activation step, the concentration of heparin varies widely between blood samples, and thus is a variable which must be accounted for in coagulation-based platelet function assays. Because heparin is highly effective in preventing and treating thrombosis and pulmonary embolism, it is commonly administered to patients as an anticoagulant in a variety of circumstances and in a wide range of medical dosages. For example, in a cardiovascular surgical situation such as a pulmonary bypass surgical operation, relatively high therapeutic dosages of anticoagulant (typically between 3.5 and 7.0 units of heparin per milliliter of blood) are administered to prevent the blood from clotting in the extracorporeal bypass circuit and in the patient's body as a result of environmental changes brought on by the surgery. The concentration of heparin in the patient's blood at any given time during this surgical operation depends on the stage of the procedure, with generally high levels present during the procedure and typically no or negligible levels prior to and following surgery. Low-dose heparin therapy, on the other hand, is used in a wide variety of clinical applications, where the clotting time of the blood must be slightly extended and confined within a relatively narrow range. Low-dose heparin treatment usually involves administering between 0.1 and 1.0 units of heparin per milliliter of blood.

Thus, to accommodate these various circumstances and heparin dosages, commercial coagulation-based platelet function assays must include a variety of test cartridge types, with the various cartridges comprising different amounts of heparin. Special test cartridges must also be produced to accommodate blood samples which contain excessive amounts of heparin, since the clotting times for these samples will frequently exceed the test period for the ACT-based analysis. To reduce the clotting time of highly heparinized blood samples, an additional reagent such as protamine is included in the test cartridge to neutralize a portion of the heparin. In addition to the extra cost associated with these multiple cartridge types, hospital and laboratory personnel must maintain a complete inventory of test cartridges, and then select the correct cartridge type for each blood sample to be analyzed. The selection and retrieval of test cartridges can be particularly inconvenient in surgical and clinical procedures which require sequential diagnostic tests, for example, during cardiopulmonary bypass surgery. For example, coagulation-based platelet function measurements are typically taken before the administration of heparin for cardiopulmonary bypass surgery to establish the patient's baseline platelet function and clotting time, and periodically throughout surgery to ensure adequate heparinization and to monitor platelet function. The ACT values can also be used to monitor the neutralization of heparin by protamine where a return to preoperative ACT is typically used as the target value. A different cartridge type is currently required to measure platelet function at these different stages of the surgical procedure.

Another deficiency with existing techniques is their inability to monitor the effectiveness of therapeutic levels of antiplatelet reagents or platelet function inhibitors in a variety of circumstances. While tests exist which can assist physicians in evaluating the efficacy of drugs and pharmacological agents at inhibiting the normal functions of platelets, none can accommodate either heparinized or unheparinized blood in a single test cartridge. In addition, interactions between heparin and antiplatelet reagents can interfere with the calculated platelet function.

A need therefore exists for an improved coagulation-based platelet function test, and particularly one based upon an improved activated clotting time test, which can accurately and reliably detect coagulation and coagulation-related activities regardless of the heparin content of the blood. The ability to measure and evaluate platelet activation and function independent of heparin concentration is important, particularly during invasive cardiac procedures in which the anticoagulant content of the blood varies significantly throughout the procedure. At the present time, there is no known single apparatus or method which is universally applicable to both heparinized and unheparinized blood. A need also exists for an improved activated clotting time test which can monitor the effectiveness of therapeutic levels of platelet function inhibitors in a variety of circumstances, regardless of the heparin content of the blood. Until this invention, no such devices or methods existed.

SUMMARY OF THE INVENTION

Accordingly, it is a general object of the present invention to provide an improved activated clotting time test.

It is a more specific object of the present invention to provide an improved activated clotting time test which can detect coagulation and coagulation-related activities, and particularly platelet function-related activities, in a blood sample regardless of the heparin concentration of the blood.

It is further an object of the present invention to provide an improved activated clotting time test which is sensitive to the functionality of platelets in a blood sample, and which can accommodate either heparinized or unheparinized blood in a single test cartridge.

It is still further an object of the present invention to provide an improved activated clotting time test which can monitor the effectiveness of therapeutic levels of antiplatelet reagents or platelet function inhibiting agents.

It is still further an object of the present invention to provide an improved activated clotting time test which can measure the effectiveness of platelet function inhibitors in a variety of circumstances, regardless of the heparin content of the blood.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, the present invention is directed to an apparatus for performing a platelet functionality test on a blood sample. The apparatus comprises a plurality of test cells, the cells being adapted for receiving an aliquot portion of the sample. Each of the cells comprises a heparin-inactivating agent, an anticoagulant agent, and a clotting reagent. At least one of the test cells further comprises a platelet activating agent. The clotting time is determined for each of the aliquot portions, and the relative clotting times of the aliquot portions in the cells are determinative of the platelet functionality of the sample.

The present invention is also directed to an apparatus for evaluating clotting characteristics of a blood sample. The apparatus comprises a plurality of test cells, the cells being adapted for receiving an aliquot portion of the sample. Each of the cells comprises a heparin-inactivating agent, an anticoagulant agent, and a clotting reagent. At least one of the test cells further comprises a platelet activating agent. The clotting time is determined for each of the aliquot portions, the relative clotting times of the aliquot portions in the cells being determinative of the clotting characteristics of the sample.

The present invention is also directed to an apparatus for performing a platelet functionality test on blood containing platelets using a plunger sensor technique. The apparatus comprises a cartridge having first and second test cells. Each test cell contains a heparin-inactivating agent, an anticoagulant agent, and a clotting reagent. The first test cell further comprises a platelet activating agent. The clotting time is determined for each of the test cells, the relative clotting times of the cells being determinative of the platelet functionality of the blood.

The present invention is further directed to a method for performing an activated clotting time test on a sample of blood containing platelets. The method comprises the steps of combining a heparin-inactivating agent, an anticoagulant agent, a clotting reagent, a platelet activating agent, and the sample of blood to be tested to form a test mixture. The platelets of the sample are activated by agitating the test mixture, and the activated clotting time test is terminated upon detecting a predetermined change in a property of the test mixture. The activated clotting time of the sample of blood is calculated based on the elapsed time.

The present invention is also directed to a method for performing an activated clotting time test on a sample of blood containing platelets using a plunger sensor apparatus. The apparatus comprises at least one test cell and a plunger assembly with n the test cell. The test cell comprises a heparin-inactivating agent, an anticoagulant agent, a clotting reagent, and a platelet activating agent. The method comprises the steps of dispensing a sample of blood into the test cell to form a test mixture, and reciprocating the plunger assembly in the test mixture by alternately lifting the plunger assembly and allowing the plunger assembly to descent through the test mixture. The point in time at which a predetermined property of the test mixture changes by a predetermined expected amount is detected by sensing the descent of the plunger assembly, the predetermined property affecting the activated clotting time test. The elapsed time from the beginning of the step of reciprocating the plunger assembly in the test mixture to the point in time at which the property of the test mixture changes by the predetermined expected amount is measured, and the activated clotting time of the sample of blood is calculated based on the elapsed time.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. In the Drawings

DETAILED DESCRIPTION OF THE PREFERRED EMBODIMENTS

To accommodate the various surgical and clinical circumstances and therapeutic heparin dosages, existing commercial coagulation-based platelet function tests that use a modified activated clotting time (ACT) test must be manufactured in a variety of test cartridge types. These various cartridges must comprise sufficient amounts of heparin to obtain accurate results or, alternatively, to accommodate blood samples which contain excessive amounts of heparin, a substance such as protamine to neutralize a portion of the excess heparin. To avoid the cost and the inconvenience associated with these multi-cartridge ACT-based tests, it was discovered that the concentration of heparin in a blood sample can be removed as a factor in ACT tests by including a standard amount of a heparin-inactivating agent such as heparinase in each test cartridge. Heparinase is a bacterial protein which catalyzes the hydrolytic degradation of heparin, but without affecting the other blood components or ACT test reagents. It was further found that, to maintain the high sensitivity associated with the use of heparin in ACT-based tests, another anticoagulant, such as argatroban (a direct thrombin inhibitor), can be included as a test reagent to accentuate the rate limiting step, thus amplifying the effects of platelet activation.

Figure 1:
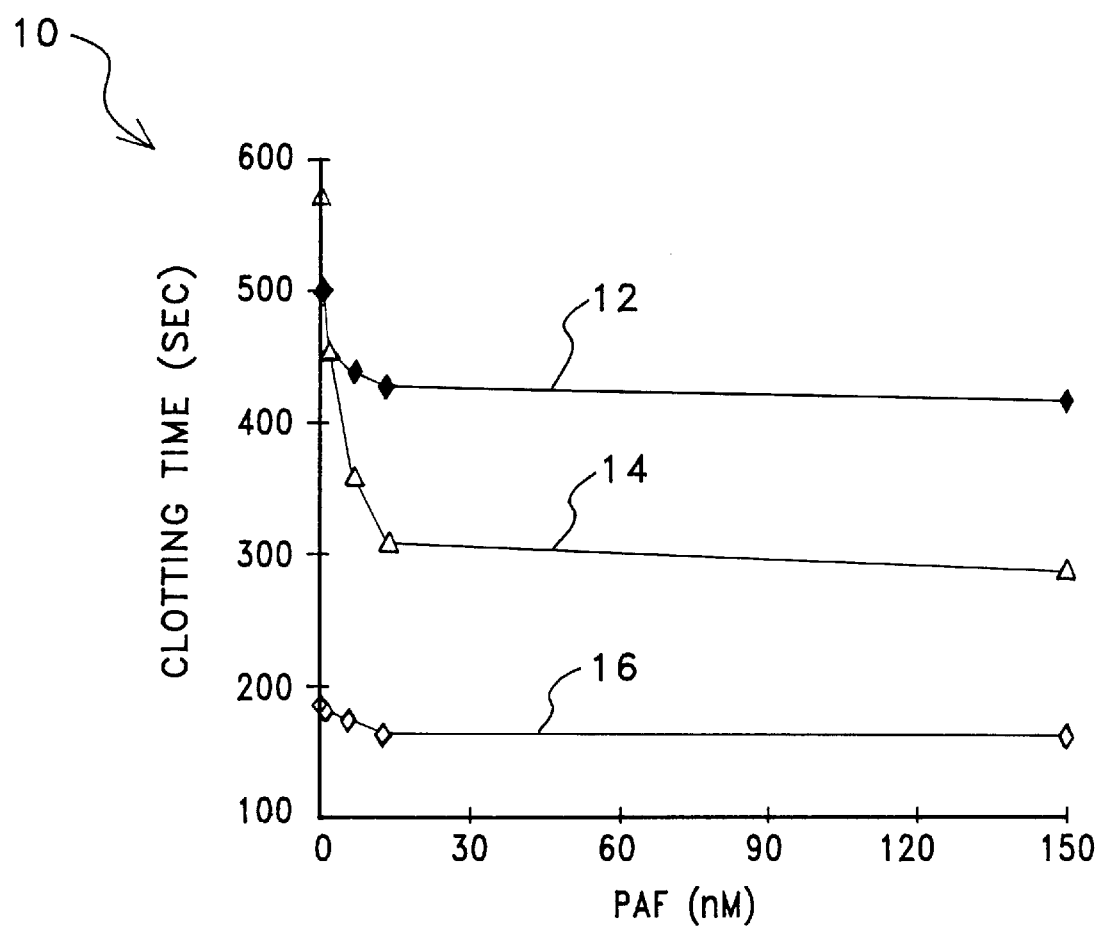
FIG. 1 is a graph of activated clotting time of fresh whole blood vs. the concentration of platelet activating factor (PAF), showing the effects of anticoagulant on clotting time. The upper curve 12 of the graph represents the behavior of a sample of blood which contains 10 μg of argatroban (anticoagulant) per milliliter of blood. The middle curve 14 represents the behavior of a blood sample which contains 3 international units (IU) of heparin (anticoagulant) per milliliter of blood. The bottom curve 16 represents the behavior of a sample of blood without anticoagulant. This is a representative graph of the behavior of the blood of one individual, but it is typically representative of the behavior of whole blood in general.

FIG. 1 presents curves 12, 14 and 16 which compare the effects of anticoagulants on the response of the activated clotting time of fresh whole blood to the concentration of platelet activating factor (PAF). Curve 12 illustrates the effects of including argatroban as an anticoagulant at a concentration of 10 $\mu$g per milliliter of blood sample. Curve 14 illustrates the effects of including heparin as an anticoagulant at a concentration of 3 IU per milliliter of blood sample. Curve 16 illustrates the effects of not including an anticoagulant as a reagent. Note that when an anticoagulant is included as a test reagent, the clotting time is significantly increased at all platelet activating factor concentrations such that the clotting time difference in the presence of the activator is increased. This provides more accurate and reliable test results, by increasing the sensitivity of the activated clotting time test.

To practice the improved ACT-based tests of the present invention, which provide high sensitivity detection of coagulation and platelet-related coagulation activities regardless of the heparin content of the blood, each of the test cells in the test cartridge includes a novel reagent composition. This novel reagent composition (shown in FIG. 8 as reagent composition 80 in reaction chamber 94) may be either a liquid or a solid powder, and includes three components: a heparin-inactivating agent, an anticoagulant agent to replace heparin, and a platelet activating agent. The heparin-inactivating agent may be any substance which selectively and rapidly inactivates heparin, thereby eliminating its anticoagulant effects. Preferably, the heparin-inactivating agent is an enzyme which is specific for heparin, such as heparinase. Heparinase is a bacterial protein which catalyzes the hydrolytic degradation of heparin. However, because of heparinase's high specificity for heparin, the enzyme does not affect the structural integrity or activity of the other blood or test components. Although heparinase is the presently preferred heparin-inactivating agent, any substance which selectively inactivates heparin without affecting the other blood or test components may be used for the practice of the invention.

The concentration of the heparin-inactivating agent required to inactivate the heparin in a blood sample will depend upon the activity of the particular heparin-inactivating agent and the concentration of heparin in the sample. However, the concentration of the heparin-inactivating agent must be sufficient to completely and rapidly inactivate any therapeutic dose of heparin, including the high therapeutic dosages typically administered during cardiovascular surgical procedures, i.e., up to about 7.0 units of heparin per milliliter of blood. With the presently preferred heparin-inactivating agent, heparinase, the reagent concentration is preferably between about 0.1 unit (U) and about 10 U, more preferably between about 1 U and about 6 U, and most preferably between about 1.5 U and about 2.5 U.

The anticoagulant agent of the reagent composition 80 accentuates the rate-limiting step in coagulation, i.e., the anticoagulant agent is included in the test mixture to amplify the effects of platelet activation on clotting time and thus increase the sensitivity of the ACT test. The anticoagulant agent may be any substance having anticoagulant activity and which is neither reactive with nor a substrate for the heparin-inactivating agent, and which is not affected by factors derived (released) from activated platelets. A wide variety of suitable anticoagulant compounds are known and readily available to the art including, for example, argatroban and other synthetic or natural compounds which are specific inhibitors of thrombin and/or clotting factor Xa. Preferably, the anticoagulant agent is a substrate-derived competitive thrombin inhibitor, such as synthetic peptides, arginine derivatives, benzamidine derivatives, and lysine derivatives. In a particularly preferred embodiment, the anticoagulant agent is the direct thrombin inhibitor, argatroban ((2R,4R)-4-methyl-1-[$N_2$-(RS)-3-methyl-1,2,3,4-tetrahydro-8-quinolinesulfonyl)-L-arginyl]-2-piperidinecarboxylic acid hydrate).

The concentration of the anticoagulant agent in reagent composition 80 required to achieve sufficient test sensitivity will depend upon the anticoagulant activity of the particular agent and the level of sensitivity desired. With the presently preferred anticoagulant agent, argatroban, the reagent concentration in the blood sample is preferably between about 0.1 $\mu$g and about 20 $\mu$g, more preferably between about 1 $\mu$g and about 15 $\mu$g, and most preferably between about 7 $\mu$g and about 12 $\mu$g per milliliter of blood sample.

The final component of the novel reagent composition 80 of the present invention is a platelet activating agent which serves as the chemical platelet activator to facilitate evaluation of the function of platelets in the blood sample to be tested. More specifically, the platelet activating agent enhances the ability of active platelets to effectively participate in the blood clotting reaction and thereby shortens the clotting time of the blood. If the platelets are inactive or not functioning normally, the platelet activating agent will have a lessened or no effect on the clotting time. Platelet activating agents are well known and readily available in the art. Suitable platelet activating agents for use in the methods and apparatus of the present invention include, without limitation, platelet activating factor (1-O-alkyl-2-acetyl-sn-glyceryl-3-phosphorylcholine, a biologically active phospholipid, commonly referred to as "PAF"), arachidonic acid, adenosine diphosphate (ADP), collagen, epinephrine, and ristocetin. In a particularly preferred embodiment, the platelet activating agent is PAF (described in Demopoulos, et al., *J. Biol. Chem.*, 254: 9355–9358 (1979)).

Figure 7:
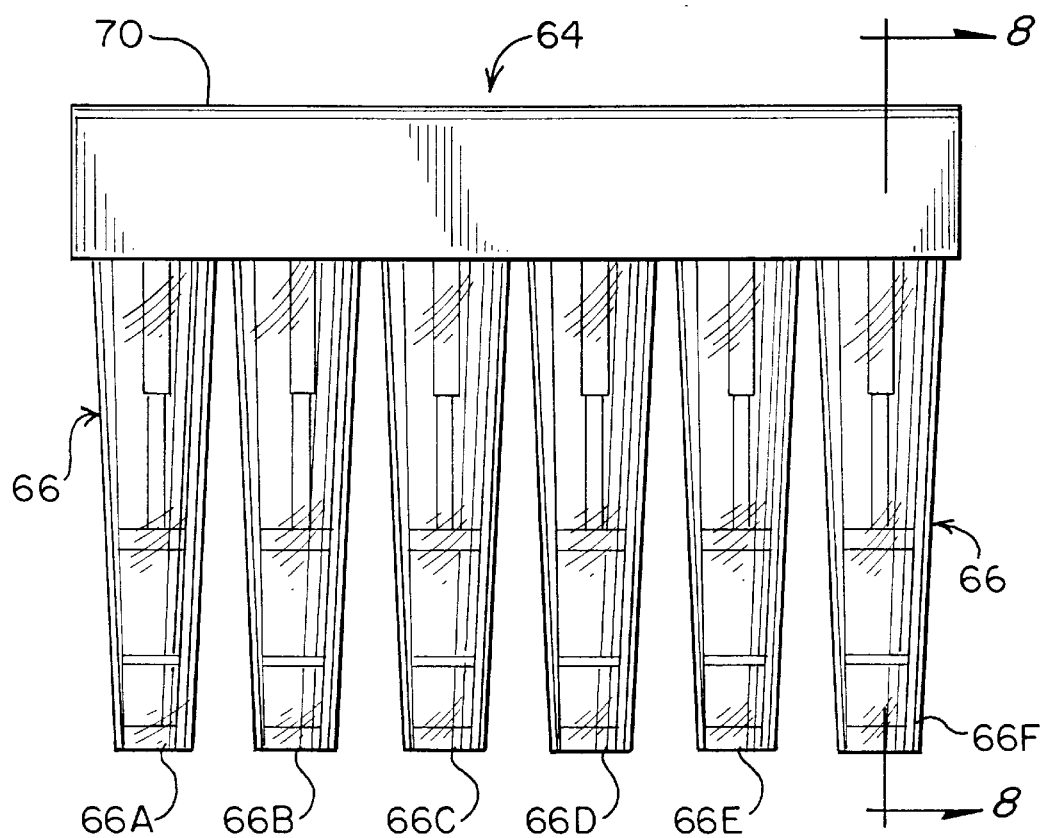
FIG. 7 is a front elevational view of the 6-channel plunger sensor cartridge shown in FIG. 6.
Figure 8:
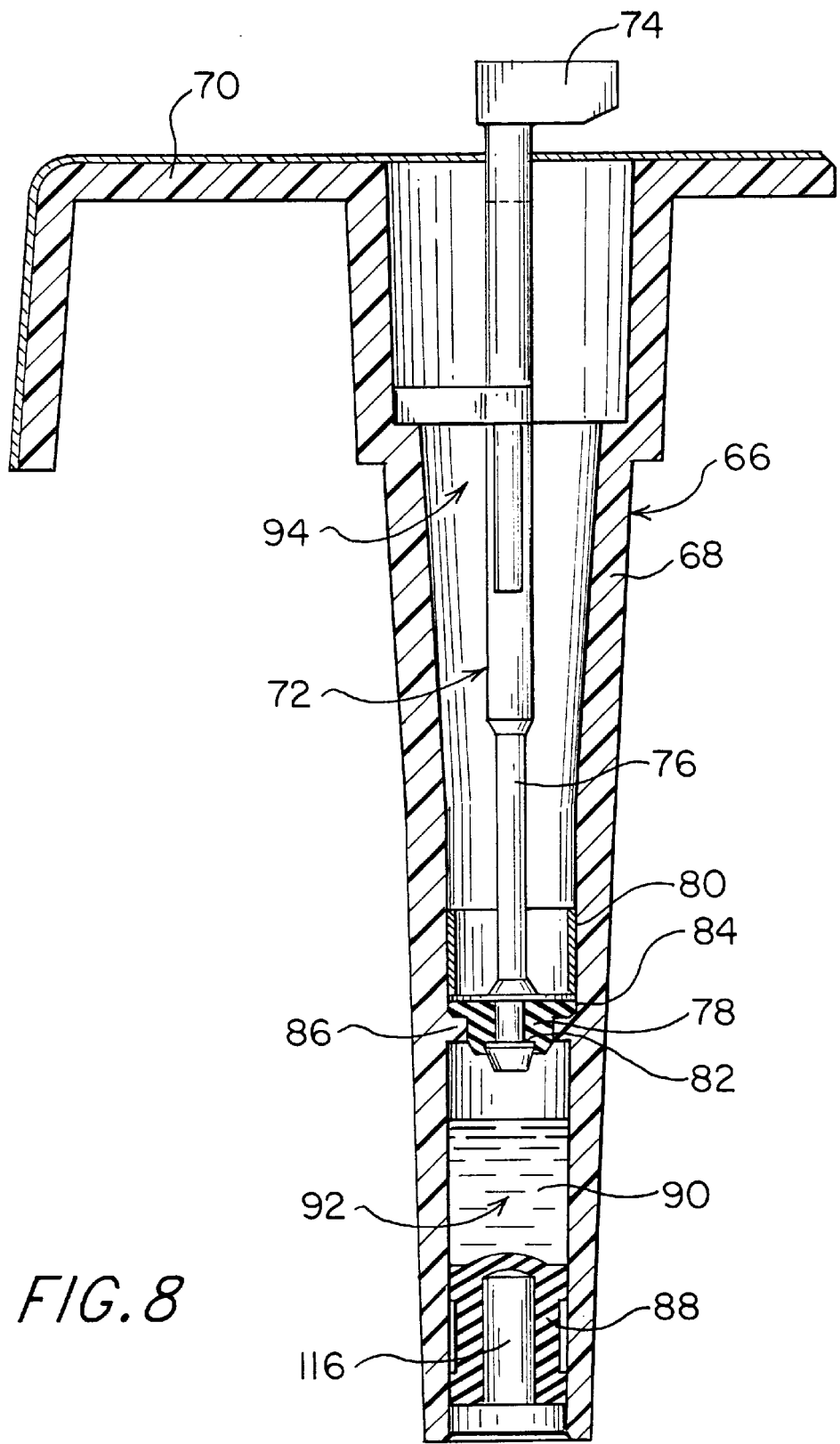
FIG. 8 is an enlarged vertical sectional view through one of the test cells of the plunger sensor cartridge, taken in the plane of line 8—8 shown in FIG. 7.

The specific concentrations of the platelet activating agent in reagent composition 80 of the present invention (i.e., reagent composition 80 in reaction chamber 94 of the test cell 66, shown in FIG. 8) will depend, in part, upon the activating efficiency of the particular agent. With the exemplified platelet activating agent, PAF, the amounts of the agent in each of the cells within the test cartridge 64, as discussed below and shown in FIGS. 6 and 7, preferably range from between zero to about 20 $\mu$g, more preferably from between zero to about 10 μg, and most preferably from between zero to about 3 μg. The final concentration of PAF in the blood sample is preferably between zero and about 10 μM, more preferably between about zero and about 1 μM, and most preferably between about zero and about 200 nM.

As discussed previously, reagent composition 80 of the present invention may be either a liquid or a solid powder, although a solid powder form (commonly referred to as a "dry fill") is preferred. To prepare reagent composition 80 as a solid or dry fill, predetermined amounts of the three components (heparin-inactivating agent, anticoagulant agent, and platelet activating agent) are combined and mixed with a saline (NaCl) solution preferably containing a protein, such as bovine serum albumin, to stabilize the platelet activating agent. The mixture may be diluted, if necessary, with additional saline solution to achieve the desired platelet activating agent concentrations. A predetermined amount of each solution of reagent composition 80 is placed in the reaction chambers 94 of the test cells 66 (shown in FIGS. 6, 7 and 8) and allowed to evaporate, leaving a solid or dry fill residue of reagent composition 80.

The modified and improved ACT test of the present invention also includes a clotting reagent in the reagent chamber (shown in FIG. 8 as reagent chamber 92) of each test cell 66. The clotting reagent (discussed below and shown in FIG. 8 as clotting reagent 90) includes an activator (commonly referred to as a surface activator), such as kaolin, to activate platelets and blood Factors XII and/or XI. However, as will be appreciated by those of skill in the art, other platelet activating reagents which function in a similar manner to kaolin may be used for the practice of the invention, such as diatomaceous earth. The clotting reagent 90 may be present in either a solid or liquid form, although the presently preferred reagent is in a liquid form. To prepare a liquid clotting reagent 90, the activator component may be dissolved in an appropriate buffered solution, a variety of which are known to those skilled in the art, including HEPES (hydroxyethyl-piperazine ethanesulfonic acid) buffer. A bacteriostatic agent such as sodium azide may also be included in clotting reagent 90. In a particularly preferred embodiment, clotting reagent 90 comprises kaolin, HEPES buffer, calcium chloride (to achieve a linear clotting time response to heparin), and sodium azide as the bacteriostatic agent. As discussed more fully below, and as illustrated in the examples hereof, an appropriate amount of clotting reagent 90 is introduced into the reagent chamber 92 of each cell of the test cartridge.

In order to provide a series of differing clotting times, at least two of the test cells comprise different amounts of the platelet activating agent. In the exemplified embodiment shown in FIG. 7, the first two cells 66A and 66B (which represent the "baseline" or non-activated clotting time) contain no platelet activating agent. Each successive cell 66C, 66D, 66E, and 66F includes increasing amounts of platelet activating agent. Although the concentrations and proportions may vary depending upon the particular reagent components (as discussed above), the following table provides an illustration of suitable amounts of the presently preferred components in reagent composition 80, prior to dilution with the blood sample:

TABLE 1

Amounts of Components in Reagent Composition 80
(Test Cartridge 64)

| Reagent | Cell 66A | Cell 66B | Cell 66C | Cell 66D | Cell 66E | Cell 66F |
|---|---|---|---|---|---|---|
| PAF | 0.0 ng | 0.0 ng | 23 ng | 116 ng | 230 ng | 2.76 μg |
| Heparinase | 2 U | 2 U | 2 U | 2 U | 2 U | 2 U |
| Argatroban | 3.5 μg | 3.5 μg | 3.5 μg | 3.5 μg | 3.5 μg | 3.5 μg |

To determine the platelet function in accordance with one embodiment of the present invention, a predetermined volume of blood to be analyzed is introduced into the reaction chamber 94 of each test cell 66A–66F, thereby dissolving reagent composition 80. The clotting reagent 90 in each reagent chamber 92 is then introduced into the corresponding reaction chamber of each test cell 66A–66F, and the clotting time is determined. The clot ratio is then calculated based on the clotting time for each test cell. Specifically, the clot ratio is defined as one minus the ratio of the average activated clotting time (e.g., cells C, D, E and F) to the average control clotting time (e.g., cells 66A and 66B). Platelet function (shown in FIG. 3) is calculated by comparing the test clot ratio to the maximum clot ratio response observed in a normal population. This value of a normal population response is known and can be used to compute the clot ratio percentage, which is in turn indicative of the platelet functionality. As will be understood by those of skill in the art, any appropriate desired calculation may be made from the relative clotting times in each cell. The platelet functionality can in turn be utilized to estimate the risk of blood loss during surgery and the need for a transfusion of blood components. The platelet functionality may further assist in managing heparin therapy during invasive cardiology procedures.

It was also discovered that platelet function can be evaluated by ACT tests in the presence of therapeutic concentrations of platelet function inhibitors, such as the IIIb/IIIa inhibitor sold under the trademark REOPRO (also referred to as "Abciximab," which is the Fab fragment of the chimeric human-murine monoclonal antibody 7E3), and regardless of the concentration of heparin in the blood to be analyzed. As discussed above, the concentration of heparin in a blood sample is removed as a factor in the ACT-based test, which may negatively impact the calculated platelet function because of the interaction between heparin and platelets, by including a standard amount of a heparin-inactivating agent in each test cell. Moreover, and also as previously discussed, the test sensitivity is significantly enhanced by including an anticoagulant other than heparin, such as argatroban which does not interact directly with platelets, in reagent composition 80 to amplify the effects of platelet activation.

In accordance with this alternate embodiment of the invention, reagent composition 180 (not shown) and clotting reagent 190 (not shown) are prepared as discussed above. However, in this embodiment, the platelet function can be calculated by comparing the clotting times of two test cells, one without a platelet activating agent (the "baseline" cell) and the other with an appropriate (preferably high) amount of platelet activating agent. Preferably, this ACT-based test is performed in duplicate, as exemplified with test cartridge 65, shown in FIG. 6. Thus, Table 2 provides an illustration of suitable concentrations of the presently preferred components in reagent composition 180 for this embodiment of the invention:

TABLE 2

Amounts of Components in Reagent Composition 180 (Test Cartridge 65)

| Reagent | Cell 66A | Cell 66B | Cell 66C | Cell 66D |
|---|---|---|---|---|
| PAF | 0.0 ng | 0.0 ng | 230 ng | 230 ng |
| Heparinase | 2 U | 2 U | 2 U | 2 U |
| Argatroban | 3.5 µg | 3.5 µg | 3.5 µg | 3.5 µg |

To determine the platelet function of a blood sample in accordance with this embodiment of the invention, the ACT test and the calculations are performed essentially as previously discussed. Again, any desired calculation may be made from the relative clotting times in each cell. The platelet functionality can in turn be utilized to assess the effectiveness of therapeutic dosages of platelet inhibitors, and to determine whether the current dosage is appropriate or optimal.

Figure 2:
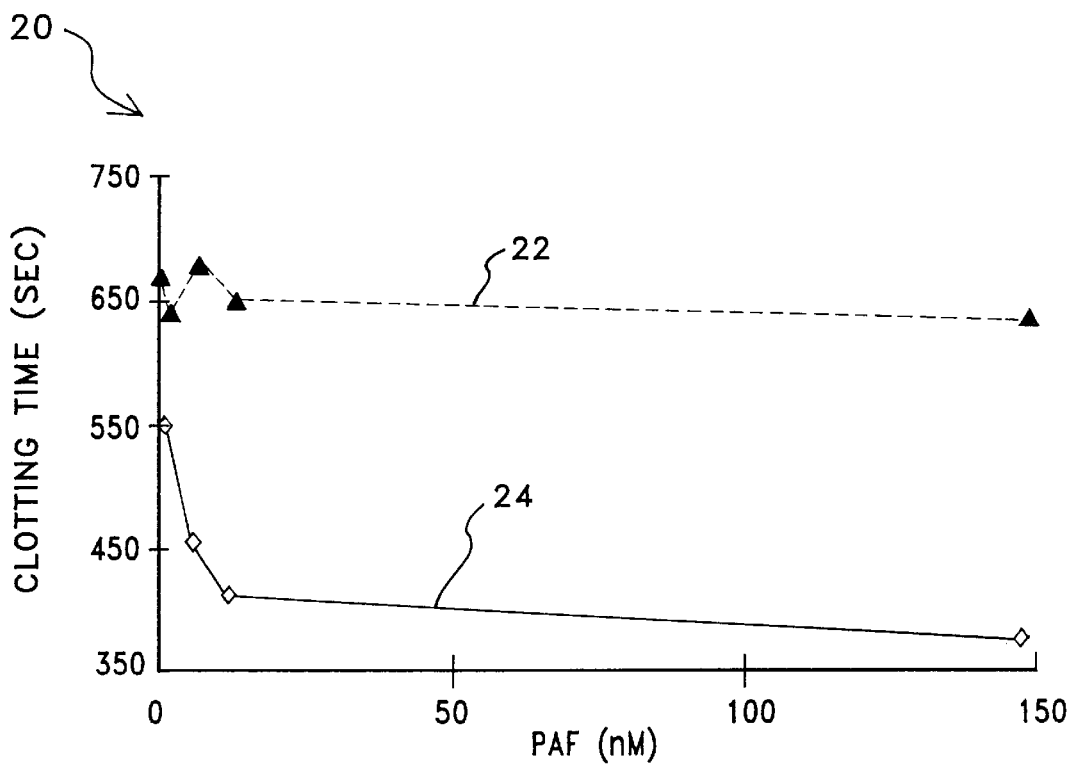
FIG. 2 is a graph of activated clotting time of fresh whole blood containing argatroban vs. the concentration of platelet activating factor, showing the effects of the platelet function inhibitor sold under the trademark REOPRO on clotting time. The upper curve 22 of the graph represents the behavior of a sample of blood which contains 10 μg of argatroban and 20 μg of ReoPro™ per milliliter of blood. The bottom curve 24 represents the behavior of the same sample of blood without the platelet function inhibitor sold under the trademark REOPRO.

Referring to FIG. 2, the effectiveness of the platelet function inhibitor sold under the trademark REOPRO (a factor IIb/IIIa inhibitor) at inhibiting platelet activation can be evaluated using argatroban as an anticoagulant. FIG. 2 presents curves 22 and 24 which compare the effects of the platelet function inhibitor sold under the trademark REOPRO on the activated clotting time of heparin-free whole blood at increasing platelet activating factor concentrations. Curve 22 illustrates the effectiveness of the platelet function inhibitor sold under the trademark REOPRO at inhibiting platelet activation at a concentration of 20 µg per milliliter of blood sample. Curve 24 illustrates the activated clotting times for the same blood sample without the platelet function inhibitor sold under the trademark REOPRO. The differences between curves 22 and 24 provide an indication of the effectiveness of the platelet function inhibitor sold under the trademark REOPRO as a platelet inhibitor for that particular blood donor. A greater difference between the ACTs of the two tests represented by the curves 22 and 24 represents a greater degree of platelet inhibition, i.e., greater sensitivity to the platelet function inhibitor sold under the trademark REOPRO.

Figure 3:
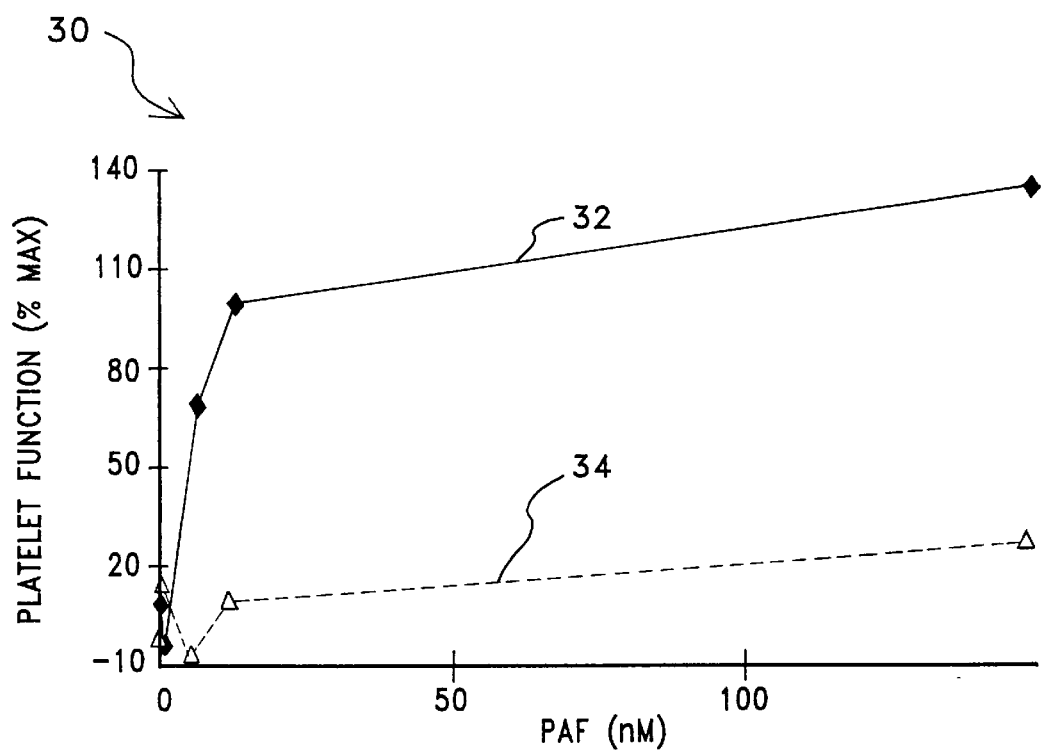
FIG. 3 is a graph of calculated platelet function vs. the concentration of platelet activating factor, showing the effects of the platelet function inhibitor sold under the trademark REOPRO. The upper curve 32 represents the behavior of a sample of blood which contains 10 μg of argatroban per milliliter of blood. The bottom curve 34 of the graph represents the behavior of the same sample of blood with argatroban and 20 μg/ml of the platelet function inhibitor sold under the trademark REOPRO per milliliter of blood.

Referring to FIG. 3, the relative effect of the platelet function inhibitor sold under the trademark REOPRO on platelet function in heparin-free whole blood also can be evaluated using argatroban as an anticoagulant. FIG. 3 presents curves 32 and 34 which compare the effects of the platelet function inhibitor sold under the trademark REOPRO on the activated clotting time of heparin-free whole blood at increasing platelet activating factor concentrations. Platelet function is expressed as a percentage of the maximum clot ratio response observed in a normal population. Curve 34 illustrates the effectiveness of the platelet function inhibitor sold under the trademark REOPRO at inhibiting platelet function at a reagent concentration of 20 µg per milliliter of blood sample. Curve 32 illustrates the platelet function of the same blood sample without the platelet function inhibitor sold under the trademark REOPRO. The differences between curves 32 and 34 demonstrate the residual platelet function of fresh whole blood containing 20 µg the platelet function inhibitor sold under the trademark REOPRO and thus provide an indication of the effectiveness of the platelet function inhibitor sold under the trademark REOPRO as a platelet inhibitor for that particular individual.

Figure 4:
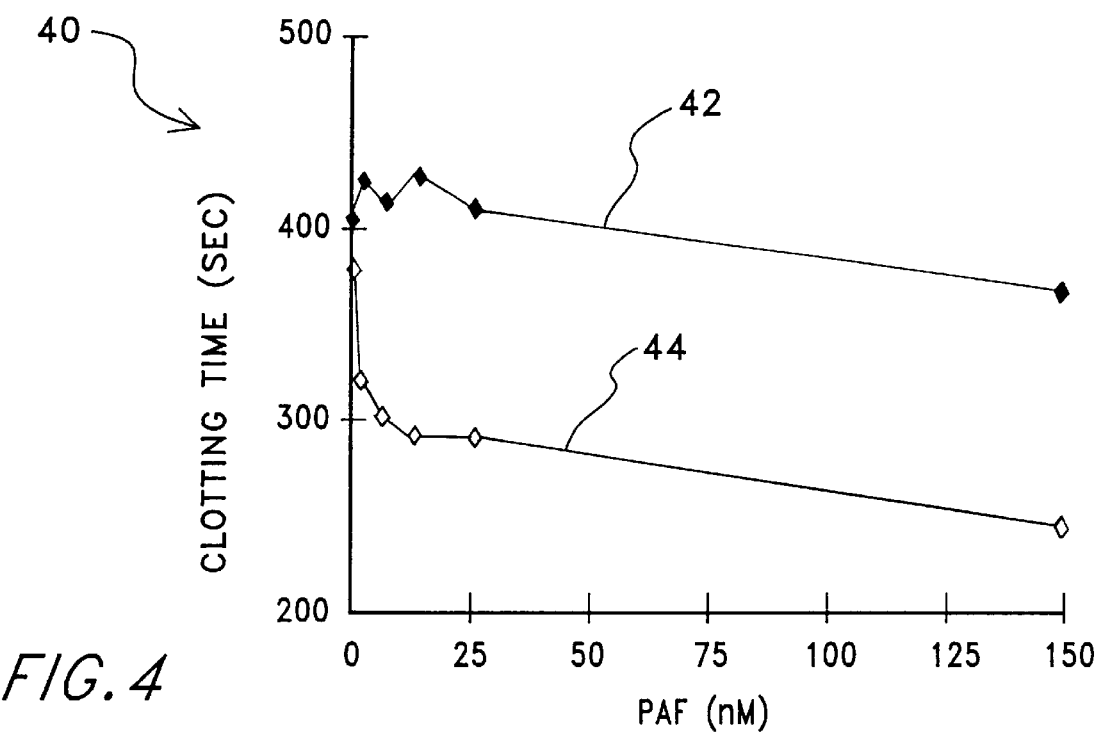
FIG. 4 is a graph of activated clotting time of fresh whole blood containing heparin vs. the concentration of platelet activating factor, showing the effects of the platelet inhibitor sold under the trademark GR 144053 on clotting time. The upper curve 42 of the graph represents the behavior of a sample of blood which contains 2 IU of heparin and 100 μM the platelet inhibitor sold under the trademark GR 144053 (a factor IIb/IIIa platelet inhibitor which inactivates the factor IIb/IIIa fibrinogen receptor on platelet surfaces). The bottom curve 44 represents the behavior of the same sample of blood without the platelet inhibitor sold under the trademark GR 144053.

This embodiment of the present invention can be extended to evaluate other types of platelet inhibitors, including other factor IIb/IIIa inhibitors. For example, as shown in FIG. 4, the effectiveness of the platelet inhibitor sold under the trademark GR 144053 (4-[4-[4-(aminoiminomethyl)phenyl]-1-piperazinyl]-1-piperidineacetic acid, hydrochloride trihydrate) at inhibiting platelet activation can be evaluated by this method. FIG. 4 presents curves 42 and 44 which compare the effects of the platelet inhibitor sold under the trademark GR 144053 on the activated clotting time of whole blood at increasing platelet activating factor concentrations. Curve 42 illustrates the effectiveness of the platelet inhibitor sold under the trademark GR 144053 at inhibiting platelet activation at a concentration of 100 µM. Curve 44 illustrates the activated clotting times for the same blood sample without the platelet inhibitor sold under the trademark GR 144053. The differences between curves 42 and 44 demonstrate the residual platelet function of whole blood containing 100 µM the platelet inhibitor sold under the trademark GR 144053 and thus is indicative of the effectiveness of this drug for the particular patient. A greater difference between the ACTs of the two tests represented by the curves 42 and 44 represents a greater degree of platelet inhibition, i.e., greater sensitivity to the platelet inhibitor sold under the trademark GR 144053.

Figure 5:
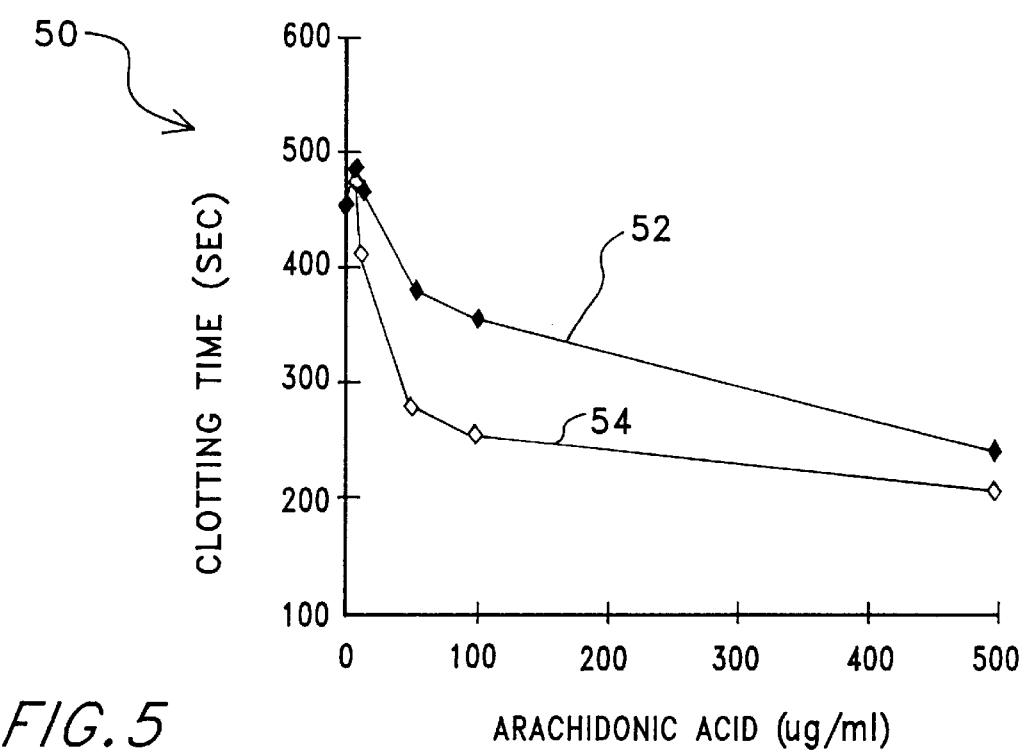
FIG. 5 is a graph of activated clotting time of fresh whole blood containing heparin vs. the concentration of arachidonic acid (a platelet activator), showing the effects of aspirin (a cyclo-oxygenase inhibitor) on clotting time. The upper curve 52 of the graph represents the behavior of a sample of blood which contains 3 IU of heparin, and which was obtained from a donor following aspirin therapy (i.e., after receiving 1 gram of aspirin per day for 3 days). The bottom curve 54 represents the behavior of blood from the same donor prior to aspirin therapy.

Referring to FIG. 5, the effectiveness of aspirin (acetylsalicylic acid), a cyclo-oxygenase inhibitor, at inhibiting platelet activation by arachidonic acid c:an be evaluated. FIG. 5 presents curves 52 and 54 which compare the effects of aspirin on the activated clotting time of whole blood at increasing arachidonic acid (platelet activator) concentrations. Curve 52 illustrates the effectiveness of aspirin at inhibiting platelet activation. The blood sample represented by curve 52 was obtained from a donor following aspirin therapy (i.e., after receiving 1 gram of aspirin per day for 3 days). Curve 54 illustrates the activated clotting times for whole blood from the same donor prior to aspirin therapy. The differences between curves 52 and 54 demonstrate the efficacy of aspirin as a platelet inhibitor, and provide an indication of the optimal therapeutic dosage for the patient.

Although this embodiment of the invention is exemplified with three different platelet function inhibitors (i.e., the platelet function inhibitor sold under the trademark REOPRO the platelet function inhibitor sold under the trademark GR 144053 and aspirin), the invention can be applied to determine the platelet function of a blood sample containing other platelet inhibitors, and to ascertain the efficacy of these inhibitors regardless of the concentration of heparin in the blood. However, as will be appreciated by those of skill in the art, to evaluate platelet function in the presence of therapeutic levels of other non-exemplified platelet inhibitors, or to evaluate the drug's effectiveness, the platelet activating agent used in the reagent composition must be properly selected to accommodate the mechanism of inhibition associated with that particular platelet inhibitor. For example, the effectiveness of the platelet function inhibitor sold under the trademark REOPRO (a factor IIb/IIIa inhibitor at inhibiting platelet activation can be evaluated using PAF as the platelet activating reagent in the reagent composition. Similarly, the effectiveness of the platelet inhibitor sold under the trademark GR 144053 (another factor IIb/IIIa inhibitor) on coagulation also can be evaluated using PAF as the activating reagent. However, for different classes of platelet inhibitors, different platelet activating agents may be appropriate. For example, as discussed above and illustrated in FIG. 5, arachidonic acid is an effective activating agent for evaluating platelet function in the presence of a cyclo-oxygenase-type platelet inhibitor, such as aspirin. When platelets are exposed to various stimuli, the platelet surface enzyme phospholipase $A_2$ is activated and this in turn cleaves arachidonic acid from membrane phospholipids. The arachidonic acid is then oxidized by cyclo-oxygenase to the endoperoxides $PGG_2$ and $PGH_2$, which leads to platelet aggregation. Aspirin inhibits platelet function by irreversibly acetylating the enzyme cyclo-oxygenase. Thus, because of the mechanism of inhibition by aspirin, arachidonic acid is an appropriate platelet activating agent for evaluating the effectiveness of aspirin therapy. As will be understood by those of skill in the art, the ACT test of the present invention can be readily modified to evaluate any platelet function inhibitor or antiplatelet agent other than those exemplified by preparing a reagent composition containing an appropriate platelet activating agent, i.e., a platelet activating agent which accommodates the inhibitory activity of the particular platelet inhibitor.

Figure 6:
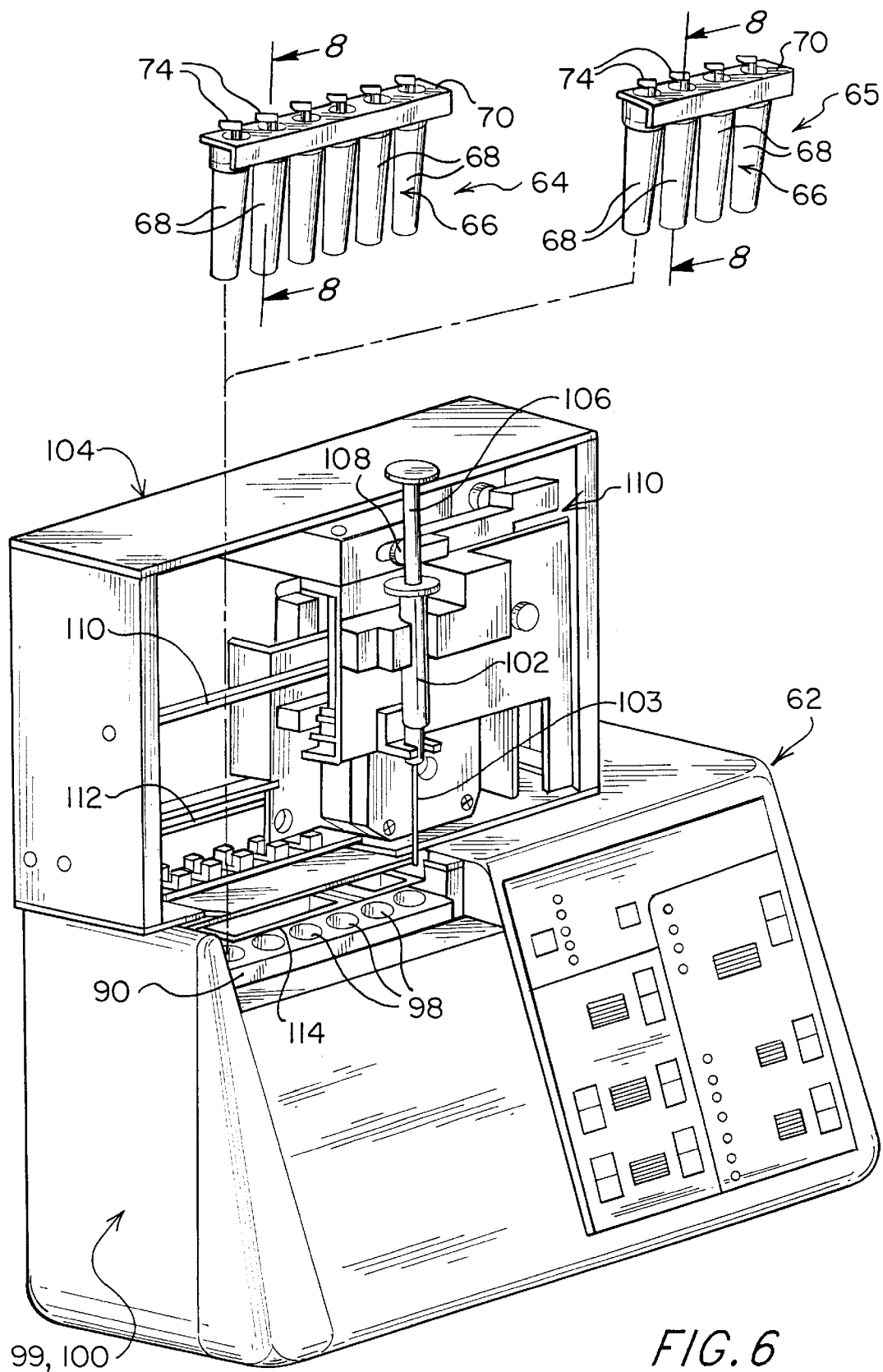
FIG. 6 is a perspective view of a 6-channel plunger sensor cartridge, a 4-channel plunger sensor cartridge, and a high sensitivity coagulation detection apparatus with which the cartridges are used on selectively alternate basis, all of which comprises an apparatus for measuring and detecting coagulation and coagulation-related factors in fluids, in accordance with the present invention.

Referring now to FIGS. 6, 7 and 8, the presently preferred embodiment of an apparatus 62 and a plunger sensor cartridge 64 may be used together in order to perform an ACT test using two unique reagents, i.e. an enzyme to degrade heparin and an anticoagulant to replace heparin. The apparatus 62 and an alternate cartridge 65 can also be used to perform a platelet inhibition test using these unique reagents. In general, the ACT test and other heparin-protamine titration tests which may be performed using the apparatus 62 and the cartridges 64, 65 have previously been described in the assignee's aforementioned patents and applications, including U.S. Pat. No. 4,599,219 and U.S. Ser. No. 08/640,275, the disclosures of which are incorporated herein by reference. Accordingly, many of the details of functionality will be generalized herein with the understanding that the assignee's prior patents and applications disclose many of these details to a greater extent. It is anticipated that coagulation-related testing techniques other than the plunger techniques may also be used to perform an ACT test and a platelet inhibition test using these novel reagents, in accordance with this invention. It is anticipated that similar results and effects as those obtained from using the assignee's plunger sensor technique will also be obtainable by practicing the present invention using other well known methods and devices.

In general, the cartridges 64, 65 as shown in FIGS. 6 and 7 include a plurality of test cells 66 (shown in FIG. 8), each of which is formed generally as a downward extending truncated tube-like member 68. Each of the tube-like members 68 is connected to an upper shelf portion 70. A plunger assembly 72 (also shown in FIG. 8) extends downward from an upper open end of each test cell 66 into the tube-like member 68. Each plunger assembly 72 includes at least one and preferably a pair of flags 74 at the upper end located at a position above the shelf portion 70. The plunger assembly 72 also includes a shaft 76 which extends from the flags 74 downward to a lower end upon which a disk member 78 is attached. The disk member 78 is formed of resilient material and includes a center, generally cylindrical main body portion 82 and an annular flange 84 located above and extending outward from the main body portion 82. The annular flange 84 includes slots or openings (not shown) formed therein at outer circumferential locations.

As shown in FIG. 8, prior to using the plunger sensor cartridge 64 or 65 in the apparatus 62, the disk member 78 is positioned with its main body portion 82 located in and sealed against an opening formed by a partition 86 extending inwardly from the tube-like member 68. The partition 86 is located between the upper and lower open ends of the tube-like member 68. A resilient flexible plug 88 is positioned in the interior of the tube-like member at its lower open end. The plug 88 seals against the inner side walls of the tube-like member 68 and confines a quantity of clotting reagent 90 (discussed above) in a reagent chamber 92 between the partition 86 and the plug 88. The clotting reagent 90 may be a liquid or a solid powder. A reaction chamber 94 is generally defined by that portion of the open tube-like member 68 above the partition 86. A predetermined amount of a reagent composition 80, the contents of which have been described in detail above, is provided in the reaction chamber 94 as either a liquid or a solid powder.

The plunger sensor cartridge 64 or 65 is inserted into a receiving block (not shown) in the apparatus 62 to conduct the ACT test. Each of the test cells 66 extends into a receptacle 98 of the receiving block. Each receptacle 98 has a configuration adapted to receive a test cell 66, while the shelf portion 70 of the cartridge 64 or 65 sits on top of the receiving block.

The apparatus 62 is generally formed of subassemblies. A dispensing subassembly 104 of the apparatus 62 automatically supplies a sample of blood to each test cell 66 of the cartridge 64 or 65. The reagent composition 80 is dissolved in the blood sample when the blood sample is introduced into the reaction chamber 94. A plunger lifting assembly 99 of the apparatus 62 controls the lifting movement of the plunger assembly 72, and a reagent drive subassembly 100 of the apparatus 62 moves the plug 88 to force the clotting reagent 90 into the reaction chamber 94, thereby mixing the clotting reagent 90 with the reagent composition 80. An optical sensing system (not shown) senses the physical descent of the plunger assembly 72 through the blood sample and reagent mixture in the reaction chamber 94 in order to detect coagulation condition.

The sample of blood is supplied to the reaction chamber 94 from a syringe 102 having a blunt needle 103 attached thereto. The syringe 102 is manually attached to the dispensing subassembly 104 of the apparatus 62. The body of the syringe 102 contains blood, preferably fresh drawn from the patient, upon which the ACT test is to be performed. Of course, prior to attachment of the syringe 102 to the dispensing subassembly 104, all air or other voids in the blood within the syringe 102 and the blunt needle 103 is removed in the conventional manner. A plunger 106 located within the body of the syringe 102 is engaged with a drive wheel 108. Rotation of the drive wheel 108 forces the syringe plunger 106 downward and expels a predetermined amount of blood from the lower end of the blunt needle 103. The extent to which the syringe plunger 106 is moved downward determines the quantity of blood expelled from the needle.

The dispensing subassembly 104 includes a movement frame 110 which is moved laterally in the horizontal direction along guide rods 112. The degree of lateral movement is controlled by the microprocessor (not shown) of the apparatus 62 in accordance with programmed information, thereby locating the blunt needle 103 directly above the open upward ends of each test cell 66 of the cartridge 64 or 65. After attaining the proper lateral location, the movement frame 110 moves the syringe 102 vertically downward to insert the lower end of the blunt needle 103 into each of the test cells 66. The desired amount of fluid sample is automatically dispensed into the test cell 66. Thereafter, the blunt needle 103 is withdrawn from the test cell 66 by the movement frame 110, and the next lateral position over a test cell 66 is assumed. The sequence again repeats itself, thereby injecting into each test cell 66 of the plunger sensor cartridge 64 or 65 that predetermined amount of blood sample needed for conducting the ACT-type test.

A portion of the plunger lifting subassembly 99 is shown in FIG. 6, and includes at least one and preferably a plurality of lift wires 114. The lift wires 114 are positioned in a lowermost location, and in that position a horizontal segment of the lift wires 114 fits underneath the flags 74 of the plunger assembly 72. Upward movement of the lift wires 114 lifts each of the plunger assemblies 72 upward, thereby removing the disk member 78 from its sealed location in the opening 84 of the partition 86. A fluid communication passageway through the opening 84 between the reagent chamber 92 and the reaction chamber 94 is thereby established. The reagent drive subassembly 100 includes a plurality of plug driver shafts 116 (shown in FIG. 8). Thereafter, or simultaneously with the upward movement of the plunger assembly 72, the plug driver shafts 116 of the reagent drive subassembly 100 move upward, forcing each plug 88 upward collapsing the reagent chamber 92 and forcing its contents 90 into the reaction chamber 94.

At the commencement of the ACT-type test, a sample of blood upon which the test is to be performed is introduced into the reaction chamber 94. The lift wires 114 of the subassembly 99 lift the plunger assembly 72 to withdraw the disk member 78 from its seated engagement with the opening in the partition 86. The plug 88 is pushed upward against the partition 86 by the plug driver shafts 116 of the subassembly 100. The clotting reagent 90 from the reagent chamber 92 is forced through the opening into the reaction chamber 94. The clotting reagent 90 is mixed with the blood and reagent mixture in the reaction chamber 94, by reciprocating the plunger assembly 72. The lift wires 114 of the subassembly 99 continue to lift the plunger assembly 72, which descends by the force of gravity through the pool of fluid in the reaction chamber 94. Throughout the test, the activation of platelets by shear stress in the blood sample is kept to a minimum, as described in U.S. Pat. No. 5,314,826. As the plunger assembly 72 descends through the fluid it is resisted by a property of the fluid in the reaction chamber 94, such as the viscosity, which changes as a result of the onset or occurrence of a coagulation-related activity, e.g., platelet activation and aggregation followed by coagulation resulting in fibrin formation. The descent rate of the plunger assembly 72 therethrough is changed, which indicates the occurrence of a coagulation-related activity. The clotting time of a blood sample is determined as described in detail in the assignee's aforementioned patents and applications, including U.S. Pat. No. 4,599,219 and U.S. Ser. No. 08/640, 275.

It will be appreciated that clinical trials may establish a quantitative correlation between platelet functionality and any medical treatment to be administered. For example, during heart bypass surgery the platelets of blood circulated in an extracorporeal circuit may become activated by the materials present in the extracorporeal circuit. Once platelets are activated they lose their ability to function further. A deficiency of functional platelets in the blood may be indicative of an increased probability of a post-operative bleeding problem. Such a deficiency, and the resulting post-operative bleeding risk, could be remedied by a transfusion of platelet concentrate. The platelet functionality test can identify a deficiency of platelets or functional platelets and aid the attending physician in ascertaining when to administer a platelet concentrate transfusion. Such a test is further useful in ascertaining the efficacy of a platelet transfusion. By performing the platelet functionality test following a platelet transfusion it is possible to determine if additional platelet concentrate transfusions are indicated. Similarly, the platelet inhibition test can assist the attending physician in evaluating the efficacy of therapeutic levels of platelet function inhibitors, and in ascertaining the optimal therapeutic dosage for the patient.

The invention is further described by the following examples which are illustrative of specific modes of practicing the invention and are not intended as limiting the scope of the invention as defined by the appended claims.

EXAMPLES

All solvents and reagents employed in the examples were used as received from the manufacturer. Bovine serum albumin (BSA) was purchased from Sigma Chemical Co. (St. Louis, Mo.; Sigma Product #A-3803); bovine lung heparin was purchased from The UpJohn Company (Kalamazoo, Mich.); heparinase was obtained from Ibex Technologies Inc. (5485 Pare, Montreal, Quebec, Canada H4P 1P7); argatroban was obtained from Mitsubishi Kasai Corp. (2-24, Higashishinagawa 2-chome, Shinagawa-ku, Tokyo 140, Japan); PAF was purchased from Sigma Chemical Co. (St. Louis, Mo.; Sigma Product #P-9525); kaolin was obtained from Charles Crystal, Inc. (St. Austell, Cornwall, UK); arachidonic acid was purchased from Helena Labs (Beaumont, Tex.); the platelet inhibitor sold under the trademark GR 144053 was obtained from Glaxo PLC (Ware, Hertfordshire, UK); and the platelet function inhibitor sold under the trademark REOPRO was obtained from Centocor BV (Leiden, The Netherlands). The coagulation detection apparatus used to perform the ACT tests in the examples was manufactured by Medtronic Hemotec, Inc. (Englewood, Colo.; Prod. No. 305-02).

Example 1
Preparation of Test Cells Comprising Reagent Composition and Clotting Reagent This example demonstrates the preparation of test cells to perform a platelet function test using an ACT-based assay which is independent of the concentration of heparin in the sample of blood, in accordance with the present invention. The procedure for preparing the test cells comprises the following steps:

1. Weigh out 4 g Kaolin. Add 5 ml of 1.0 M calcium chloride solution. Dilute mixture to 100 ml with hydroxyethyl-piperazine ethanesulfonic acid (HEPES) buffer. This provides 4% w/v suspension of kaolin in HEPES buffer, 0.05 M calcium, pH 7.3. Add 0.088 ml of this kaolin mixture into the reagent chamber 92 of each cell 66 in the test cartridge.
2. Weigh out 62.5 mg BSA
3. Weigh out 219 mg NaCl
4. Make up to 25 ml with deionized water. This gives 0.25 % BSA/0.15 M NaCl. Allow BSA to completely dissolve.
5. Using a Hamilton syringe, pipette 50 $\mu$l platelet activating factor (PAF) into a clean vial and allow the chloroform solvent to evaporate. Add 2 ml BSA/NaCl solution and stir continuously for at least 1 hour. This provides a 100 $\mu$M working stock of PAF.

6. Dilute the working stock PAF serially down to 87.5 nM with BSA/NaCl solution. 5 μl of these solutions gives 1.25 nM, 6.25 nM, 12.5 nM and 150 nM in 0.35 ml test sample.
7. Weigh out 7 mg argatroban. Add 9.5 m. 0.15 M NaCl and acidify with 0.1 M HCl to dissolve the argatroban. Increase pH to 7.4 with 0.1 M NaOH. Bring volume up to 10 ml with NaCl solution. This gives a solution of 700 μg/ml. 5 μl of this solution in each cell gives 10 μg/ml in 0.35 ml test sample.
8. Heparinase solutions are made to 100 IU/ml in 5% w/v trehalose. 20 μl of this solution is added to each cell to give 2 IU in 0.35 ml test sample.
9. The following amounts are added to the reaction chamber 94 of the cells 66, and result in the indicated blood concentration:

| Cell | Reagent added | Concentrations |
| --- | --- | --- |
| A | 5 μl BSA/NaCl | 0 nM |
|  | 5 μl 700 μg/ml argatroban | 10 μg/ml |
|  | 20 μl 100 IU/ml heparinase | 2 IU/cell |
| B | 5 μl BSA/NaCl | 0 nM |
|  | 5 μl 700 μg/ml argatroban | 10 μg/ml |
|  | 20 μl 100 IU/ml heparinase | 2 IU/cell |
| C | 5 μl 87.5 nM PAF | 1.25 nM |
|  | 5 μl 700 μg/ml argatroban | 10 μg/ml |
|  | 20 μl 100 IU/ml heparinase | 2 IU/cell |
| D | 5 μl 437.5 nM PAF | 6.25 nM |
|  | 5 μl 700 μg/ml argatroban | 10 μg/ml |
|  | 20 μl 100 IU/ml heparinase | 2 IU/cell |
| E | 5 μl 875 nM PAF | 12.5 nM |
|  | 5 μl 700 μg/ml argatroban | 10 μg/ml |
|  | 20 μl 100 IU/ml heparinase | 2 IU/cell |
| F | 5 μl 10.5 μM PAF | 150 nM |
|  | 5 μl 700 μg/ml argatroban | 10 μg/ml |
|  | 20 μl 100 IU/ml heparinase | 2 IU/cell |

10. The water is allowed to evaporate, leaving a dry fill in each cell.
11. Using a sample of normal blood from a voluntary donor, and a cartridge prepared as described above, 0.35 ml aliquots of blood are added to each cell and the clotting time of the blood in each cell is determined and plotted as previously described.

The titration curve can be normalized by converting the clotting times to ratios. The average clotting time of Cell A and Cell B, with no platelet activating factor present, is the cell clotting time to which all other cell clotting times are compared. The ratio is calculated by dividing the average of Cell A and Cell B clotting time in seconds by each other cell clotting time in seconds. A clot ratio is then calculated as 1 minus the ratio of the average of Cell A and Cell B clotting time to other cell clotting times (1−average of CellA&Btime/CellXtime). Data can also be presented in terms of platelet function as a percentage of normal. This is calculated from the clot ratio by multiplying the clot ratio by 100 and then by a factor of 3.74 which has been determined by measuring the maximum platelet activating factor response from at least 20 normal donors. These donors had no known platelet dysfunction and were taking no known medications.

The test cartridge and method described herein are useful for providing a simple and rapid point-of-care platelet function assay. This assay can identify patients with low platelet function. This is useful for those patients with excessive post-cardiopulmonary bypass blood loss (due to a platelet-related disorder) so that appropriate platelet transfusion can be administered. In addition, those patients experiencing excessive post-cardiopulmonary bypass blood loss who are found to have normal platelet function can be treated appropriately, thus avoiding the need for expensive platelet therapy and the health risks associated with blood component transfusion.

Example 2
Preparation of Test Cells for Evaluating Platelet Function of Whole Blood Comprising REOPRO™ Platelet Inhibitor.

This example demonstrates the preparation of test cells to perform a platelet function test using an ACT-based assay on blood containing the platelet function inhibitor sold under the trademark REOPRO and which is independent of the concentration of heparin in the blood sample. The test cells were prepared essentially as described above in Example 1, except that step 11 was modified as follows:

11. Two samples of blood were obtained from a normal donor, one collected into 3 IU/ml heparin and the other collected into 3 IU/ml heparin containing 20 μg/ml the platelet function inhibitor sold under the trademark REOPRO. Both samples were incubated for 10 minutes at 37° C., then 0.35 ml aliquots of blood were added to each cell and the clotting time of the blood in each cell was determined and plotted as shown in FIG. 2. Data can also be presented in terms of platelet function as a percentage of normal. This is calculated from the clot ratio by multiplying the clot ratio by 100 and then by a factor of 3.74 which has been determined by measuring the maximum platelet activating factor response from at least 20 donors. These donors had no known platelet dysfunction and were not taking any known medication. The results of platelet function as a percentage of normal is shown in FIG. 3.

Example 3
Preparation of Test Cells for Evaluating Platelet Function of Whole Blood Comprising GR 144053 Platelet Inhibitor.

This example demonstrates the preparation of test cells to perform an ACT-based test on blood containing the platelet inhibitor sold under the trademark GR 144053 platelet inhibitor, and which is independent of the concentration of heparin in the blood sample. The test cells were prepared essentially as described above in Example 1, except that steps 7 and 8 were omitted, and steps 9 through 11 were modified as follows:

9. The following amounts were added to the cells and resulted in the indicated blood concentrations:

| Cell | Reagent added | Concentrations |
| --- | --- | --- |
| A | 5 μl BSA/NaCl | 0 nM |
| B | 5 μl BSA/NaCl | 0 nM |
| C | 5 μl 87.5 nM PAF | 1.25 nM |
| D | 5 μl 437.5 nM PAF | 6.25 nM |
| E | 5 μl 875 nM PAF | 12.5 nM |
| F | 5 μl 10.5 nM PAF | 150 nM |

10. The water was allowed to evaporate, leaving a dry fill in each cell.
11. Two samples of blood were obtained from a normal donor, one collected into 3 IU/ml heparin and the other collected into 3 IU/ml heparin containing 100 μM the platelet inhibitor sold under the trademark GR 144053. Both samples were incubated for 10 minutes, then 0.35 ml aliquots of blood were added to each cell and the clotting time of the blood in each cell was determined and plotted as shown in FIG. 4.

Example 4
Preparation of Test Cells for Evaluating Platelet Function of Whole Blood from Donor Before and After Aspirin Therapy This example demonstrates the preparation of test cells to perform an ACT-based test on blood obtained from a donor before and after aspirin (cyclo-oxygenase inhibitor) therapy, and which is independent of the concentration of heparin in the blood sample. The procedure for preparing the test cells comprises the following steps:

1. Weigh out 4 g Kaolin. Add 5 ml of 1.0 M calcium chloride solution. Dilute the mixture to 100 ml with hydroxyethyl-piperazine ethanesulfonic acid (HEPES) buffer. This provides 4% w/v suspension of kaolin in HEPES buffer, 0.05 M calcium, pH 7.3. Add 0.088 ml of this kaolin mixture into the reagent chamber 92 of each cell 66 in the test cartridge.
2. Combine 5 mg arachidonic acid and 9 mg NaCl. Dilute to 1 ml with deionized water. This provides a 5000 μg/ml solution of arachidonic acid.
3. Using a Hamilton syringe, pipette the following reagent amounts into the cells of the test cartridge to produce the indicated blood concentrations:

| Cell | Reagent added | Concentrations |
|---|---|---|
| A | 5 μl NaCl | 0 μg/ml |
| B | 0.7 μl 5 mg/ml arachidonate | 10 μg/ml |
| C | 1.4 μl 5 mg/ml arachidonate | 20 μg/ml |
| D | 3.5 μl 5 mg/ml arachidonate | 50 μg/ml |
| E | 7 μl 5 mg/ml arachidonate | 100 μg/ml |
| F | 35 μl 5 mg/ml arachidonate | 500 μg/ml |

4. The water was allowed to evaporate, leaving a dry fill in each cell.
5. Two samples of blood were obtained from a normal donor, one collected into 3 IU/ml heparin prior to aspirin therapy and the other collected into 3 IU/ml heparin and taken from the same donor after 3 days of aspirin therapy (1 g per day, orally). 0.35 ml aliquots of blood were added to each cell and the clotting time of the blood in each cell was determined and plotted as shown in FIG. 5.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

We claim:

1. An apparatus for performing a platelet functionality test on a blood sample, said apparatus comprising a plurality of test cells, each of said cells comprising a reaction chamber for receiving an aliquot portion of said sample, wherein each of said cells comprises a heparin-inactivating agent, an anticoagulant agent and a sufficient amount of a clotting reagent to achieve clotting, and wherein at least one of the cells comprises a platelet activating agent, wherein said platelet activating agent is a reagent other than said clotting reagent.

2. The apparatus as defined in claim 1, wherein the heparin-inactivating agent is an enzyme specific for heparin.

3. The apparatus as defined in claim 2, wherein the enzyme is heparinase.

4. The apparatus as defined in claim 1, wherein the heparin-inactivating agent is present at a concentration of between about 0.1. and about 10 international units per milliliter of blood sample.

5. The apparatus as defined in claim 1, wherein the heparin-inactivating agent is present at a concentration of between about 1.5 and about 2.5 international units per milliliter of blood sample.

6. The apparatus as defined in claim 1, wherein the heparin-inactivating agent is present at a concentration of between about 1.5 and about 2.5 international units per milliliter of blood sample.

7. The apparatus as defined in claim 1, wherein the anticoagulant agent is an inhibitor of at least one of Factor Xa and Factor II.

8. The apparatus as defined in claim 1, wherein the anticoagulant agent is a substrate-derived competitive thrombin inhibitor.

9. The apparatus as defined in claim 1, wherein the anticoagulant agent is a thrombin inhibitor selected from the group consisting of synthetic peptides, arginine derivatives, benzamidine derivatives, and lysine derivatives.

10. The apparatus as defined in claim 1, wherein the anticoagulant agent is argatroban.

11. The apparatus as defined in claim 1, wherein the anticoagulant agent is present at a concentration of between about 0.1 μg and about 20 μg per milliliter of blood sample.

12. The apparatus as defined in claim 1, wherein the anticoagulant agent is present at a concentration of between about 1 μg and about 15 μg per milliliter of blood sample.

13. The apparatus as defined in claim 1, wherein the anticoagulant agent is present at a concentration of between about 7 μg and about 12 μg per milliliter of blood sample.

14. The apparatus as defined in claim 1, wherein the clotting reagent is an activator of at least one of Factor XII and Factor XI.

15. The apparatus as defined in claim 1, wherein the clotting reagent is kaolin or diatomaceous earth.

16. The apparatus as defined in claim 1, wherein the clotting reagent is kaolin.

17. The apparatus as defined in claim 1, wherein the platelet activating agent is selected from the group consisting of 1-O-alkyl-2-acetyl-sn-glyceryl-3-phosphorylcholine, arachidonic acid, collagen, epinephrine, and ristocetin.

18. The apparatus as defined in claim 1, wherein the platelet activating agent is 1-O-alkyl-2-acetyl-sn-glyceryl-3-phosphorylcholine.

19. The apparatus as defined in claim 1, wherein the platelet activating agent in the blood sample is present at a concentration of between 0 and about 10 μM.

20. The apparatus as defined in claim 1, wherein the platelet activating agent in the blood sample is present at a concentration of between 0 and about 1.0 μM.

21. The apparatus as defined in claim 1, wherein the platelet activating agent in the blood sample is present at a concentration of between 0 and about 200 nM.

22. The apparatus as defined in claim 1, wherein the platelet functionality test is performed using a plunger sensor technique.

23. The apparatus as defined in claim 1, wherein the blood comprises a therapeutic amount of a platelet function inhibitor.

24. The apparatus as defined in claim 1, wherein the platelet function inhibitor is selected from the group consisting of Abciximab, 4-[4-[4-(aminoiminomethyl)phenyl]-1-piperazinyl]-1-piperidineacetic acid, hydrochloride trihydrate, and acetylsalicylic acid.

25. The apparatus as defined in claim 1, wherein the platelet function inhibitor is Abciximab, and wherein the platelet activating agent is 1-O-alkyl-2-acetyl-sn-glyceryl-3-phosphorylcholine.

26. The apparatus as defined in claim 1, wherein the platelet function inhibitor is 4-[4-[4-(aminoiminomethyl)phenyl]-1-piperazinyl]-1-piperidincacetic acid, hydrochloride trihydrate, and wherein the platelet activating agent is 1-O-alkyl-2-acetyl-sn-glyceryl-3-phosphorylcholine.

27. The apparatus as defined in claim 1, wherein the platelet function inhibitor is acetylsalicylic acid, and wherein the platelet activating agent is arachidonic acid.

28. An apparatus for performing a platelet functionality test on blood containing platelets using a plunger sensor technique, said apparatus comprising a cartridge having first and second test cells, each test cell containing a heparin-inactivating agent, an anticoagulant agent, and a sufficient amount of a clotting reagent to achieve clotting, and wherein said first test cell further comprises a platelet activating agent, wherein said platelet activating agent is a reagent other than said clotting reagent, and wherein a relative clotting time is determined for said first test cell as compared to said second test cell, and wherein the relative clotting time of said first cell is determinative of the platelet functionality of said blood.

29. The apparatus as defined in claim 28, wherein the heparin-inactivating agent is heparinase.

30. The apparatus as defined in claim 28, wherein the anticoagulant agent is a thrombin inhibitor selected from the group consisting of synthetic peptides, arginine derivatives, benzamidine derivatives and lysine derivatives.

31. The apparatus as defined in claim 28, wherein the anticoagulant agent is argatroban.

32. The apparatus as defined in claim 28, wherein the clotting reagent is kaolin.

33. The apparatus as defined in claim 28, wherein the platelet activating agent is 1-O-alkyl-2-acetyl-sn-glyceryl-3-phosphorylcholine or arachidonic acid.

34. The apparatus as defined in claim 28, wherein the platelet activating agent is 1-O-alkyl-2-acetyl-sn-glyceryl-3-phosphorylcholine.

35. The apparatus as defined in claim 29, wherein the heparinase is present at a concentration of between about 1.5 and about 2.5 units per milliliter of blood.

36. The apparatus as defined in claim 31, wherein the argatroban is present at a concentration of between about 7 $\mu$g and about 12 $\mu$g per milliliter of blood sample.

37. The apparatus as defined in claim 34, wherein the 1-O-alkyl-2-acetyl-sn-glyceryl-3-phosphorylcholine in the blood is present at a concentration of between 0 and about 1.0 $\mu$M.

\* \* \* \* \*